(12) United States Patent
Miki

(10) Patent No.: US 9,903,812 B2
(45) Date of Patent: Feb. 27, 2018

(54) OPTICAL OBSERVATION APPARATUS AND OPTICAL OBSERVATION METHOD

(71) Applicant: MITUTOYO CORPORATION, Kawasaki, Kanagawa (JP)

(72) Inventor: Yutaka Miki, Tokyo (JP)

(73) Assignee: MITUTOYO CORPORATION, Kawasaki (JP)

( * ) Notice: Subject to any disclaimer, the term of this patent is extended or adjusted under 35 U.S.C. 154(b) by 75 days.

(21) Appl. No.: 14/835,229

(22) Filed: Aug. 25, 2015

(65) Prior Publication Data

US 2016/0061724 A1    Mar. 3, 2016

(30) Foreign Application Priority Data

Sep. 2, 2014   (JP) .................. 2014-178284

(51) Int. Cl.
*G01N 21/47*     (2006.01)
*G01B 11/24*     (2006.01)

(52) U.S. Cl.
CPC .......... *G01N 21/474* (2013.01); *G01B 11/24* (2013.01); *G01N 2021/4709* (2013.01); *G01N 2021/4742* (2013.01)

(58) Field of Classification Search
CPC ......... G01N 21/474; G01N 2021/4709; G01N 202/4742; G01B 11/24
See application file for complete search history.

(56) References Cited

U.S. PATENT DOCUMENTS

2006/0114473 A1* 6/2006 Tearney ............... A61B 5/0066
                                                                      356/479
2012/0019821 A1* 1/2012 Chen .................. G02B 21/0032
                                                                      356/303

FOREIGN PATENT DOCUMENTS

JP    2008-032668 A    2/2008
JP    2008-032951 A    2/2008

* cited by examiner

*Primary Examiner* — Hina F Ayub
*Assistant Examiner* — Amanda Merlino
(74) *Attorney, Agent, or Firm* — Oliff PLC

(57) ABSTRACT

Optical observation apparatus includes: light source emitting broadband light; image fiber with first and second end faces, wherein end faces of plural cores are two-dimensionally arrayed in first and second end faces; imaging optical system provided on first end face side of image fiber, causing light from first end face to be imaged on imaging plane; and axial aberration optical system provided on second end face side of image fiber, having an axial chromatic aberration on optical axis, and causing light from second end face toward object to be observed to be converged. Image fiber takes light from light source from first end face, and transmits light to second end face, and takes light, reflected and scattered by a surface of object, converged by axial aberration optical system, and focused for each plural core on second end face, from second end face and transmits light to first end face.

5 Claims, 5 Drawing Sheets

OPTICAL OBSERVATION APPARATUS AND OPTICAL OBSERVATION METHOD

CROSS-REFERENCE TO RELATED APPLICATION

This non-provisional application claims priority under 35 U.S.C. § 119 (a) from Japanese Patent Application No. 2014-178284, filed on Sep. 2, 2014, the entire contents of which are incorporated herein by reference.

BACKGROUND

Technical Field

The present invention relates to an optical observation apparatus and an optical observation method of observing a surface of an object to be observed by receiving reflected light and scattered light of light irradiated onto the surface of the object to be observed.

When an object to be observed (a work) having irregularities is observed by a microscope or the like, it is not easy to obtain an observation image well-focused in a wide range of an observation plane of the work. In particular, in the case of observation optically at a high magnification, a focal depth of a lens is shallow, and thus, the observation is further difficult.

Meanwhile, in a case where an all-in-focus image, in which the entire plane of the face to be observed is well-focused, is obtained when the work having irregularities is observed by the microscope or the like, it is often hard to understand the height of each portion of the irregularities of the work. For example, in some cases, it is hard to grasp whether the observed portion is a convex portion or a concave portion.

JP-A 2008-32951 discloses a configuration in which a test subject is irradiated with monochromatic light of three colors, and detection data, read from a light detection section for each monochromatic light of three colors, are synthesized, thereby obtaining a color image of the test subject. In addition, JP-A 2008-32668 discloses a scanning type shape measuring machine provided with a point light source that includes a plurality of wavelengths, a lens that generates an axial chromatic aberration and an optical scanner that performs angle-scanning of light. In this machine, an object having irregularities on a surface thereof is scanned with light, and inspection of a position or a height on the surface is performed by receiving reflected light.

SUMMARY OF THE INVENTION

However, as described in JP-A 2008-32951, in the configuration of obtaining the color image by taking the detection data for each monochromatic light of three colors, and synthesizing the data, it is necessary to perform a complex image processing. In addition, as described in JP-A 2008-32668, in the configuration of scanning a position or a height on the surface by performing irradiation and scanning by causing the point light source to be directed to the object, it is possible to obtain an image well-focused in the entire surface of the object, but there still remains a problem that it is hard to visually recognize the irregularities of the surface.

An object of the present invention is provide an optical observation apparatus and an optical observation method capable of easily acquiring an all-in-focus image of an object to be observed, and further visually grasping a height of each portion of a surface.

In order to solve the problems described above, an optical observation apparatus of the present invention is provided with: a light source emitting broadband light; an image fiber with a first end face and a second end face, in which end faces of a plurality of cores are two-dimensionally arrayed in the first end face and the second end face; an imaging optical system provided on the first end face side of the image fiber, and causing light emitted from the first end face to be imaged on an imaging plane; and an axial aberration optical system provided on the second end face side of the image fiber, having an axial chromatic aberration on an optical axis, and causing light emitted from the second end face toward an object to be observed to be converged. The image fiber takes the light emitted from the light source from the first end face, and transmits the light to the second end face, and takes the light, which is reflected and scattered by a surface of the object to be observed, converged by the axial aberration optical system, and focused for each of the plurality of cores on the second end face, from the second end face and transmits the light to the first end face.

According to such a configuration, the broadband light emitted from the light source is transmitted from the first end face to the second end face of the image fiber, and is irradiated onto the object to be observed from the second end face via the axial aberration optical system. The broadband light is converged at a focal length depending on a wavelength by the axial aberration optical system. Accordingly, the focal length depending on the wavelength of the light focused on the surface among the light irradiated onto the object to be observed, and a height of the surface of the object to be observed are associated with each other. The image fiber takes the light focused for each of the plurality of cores on the second end face among the light reflected and scattered by the surface of the object to be observed, and transmits the taken light to the first end face. The light taken from each of the cores of the second end face containing components of the reflected and scattered light, by the surface of the object to be observed, of the focused light. Thus, the light taken from each of the cores of the second end face, transmitted to the first end face, and projected on the imaging plane by the imaging lens appears as an image containing a wavelength component depending on the height of the object to be observed.

In the optical observation apparatus of the present invention, the axial aberration optical system may cause light, with a wavelength to be focused onto the surface of the object to be observed among light emitted from each of the plurality of cores and reflected and scattered by the surface of the object to be observed, to be imaged on the core of an emission source on the second end face. According to such a configuration, it is possible to transmit the light imaged on the second end face to the first end face, and project the image on the imaging plane by the imaging lens, and thus, it is possible to obtain a sharp image of the object to be observed.

In the optical observation apparatus of the present invention, the imaging optical system may cause the light with a wavelength, which corresponds to a distance between the axial aberration optical system and the object to be observed, to be imaged on the imaging plane. According to such a configuration, a display distinguishable according to wavelength (color) depending on the height of the surface of the object to be observed is performed as the image appearing on the imaging plane.

In the optical observation apparatus of the present invention, the light source may be a white light source. According to such a configuration, it is possible to grasp the height of the object to be observed in a range of wavelengths included in white light emitted from the white light source.

An optical observation method of the present invention includes: irradiating an object to be observed with broadband light by an axial aberration optical system having an axial chromatic aberration; taking, by an image fiber with a first end face and a second end face in which end faces of a plurality of cores are two-dimensionally arrayed in the first end face and the second end face, light which is reflected and scattered by a surface of the object to be observed, converged by the axial aberration optical system, and focused for each of the plurality of cores on the second end face, and transmitting the taken light to the first end face; and causing light emitted from the first end face to be imaged on an imaging plane by an imaging optical system.

According to such a configuration, the object to be observed is irradiated with the broadband light by the axial aberration optical system. Further, the light is converged at a focal length depending on a wavelength by the axial aberration optical system. Accordingly, the focal length depending on the wavelength of the light focused on the surface among the light irradiated onto the object to be observed, and a height of the surface of the object to be observed are associated with each other. The image fiber takes the light focused for each of the plurality of cores on the second end face among the light reflected and scattered by the surface of the object to be observed, and transmits the taken light to the first end face. The light taken from each of the cores of the second end face containing components of the reflected and scattered light, by the surface of the object to be observed, of the focused light. Thus, the light taken from each of the cores of the second end face, transmitted to the first end face, and projected on the imaging plane by the imaging lens appears as an image containing a wavelength component depending on the height of the object to be observed.

DETAILED DESCRIPTION OF THE EMBODIMENTS

Figure 1A:
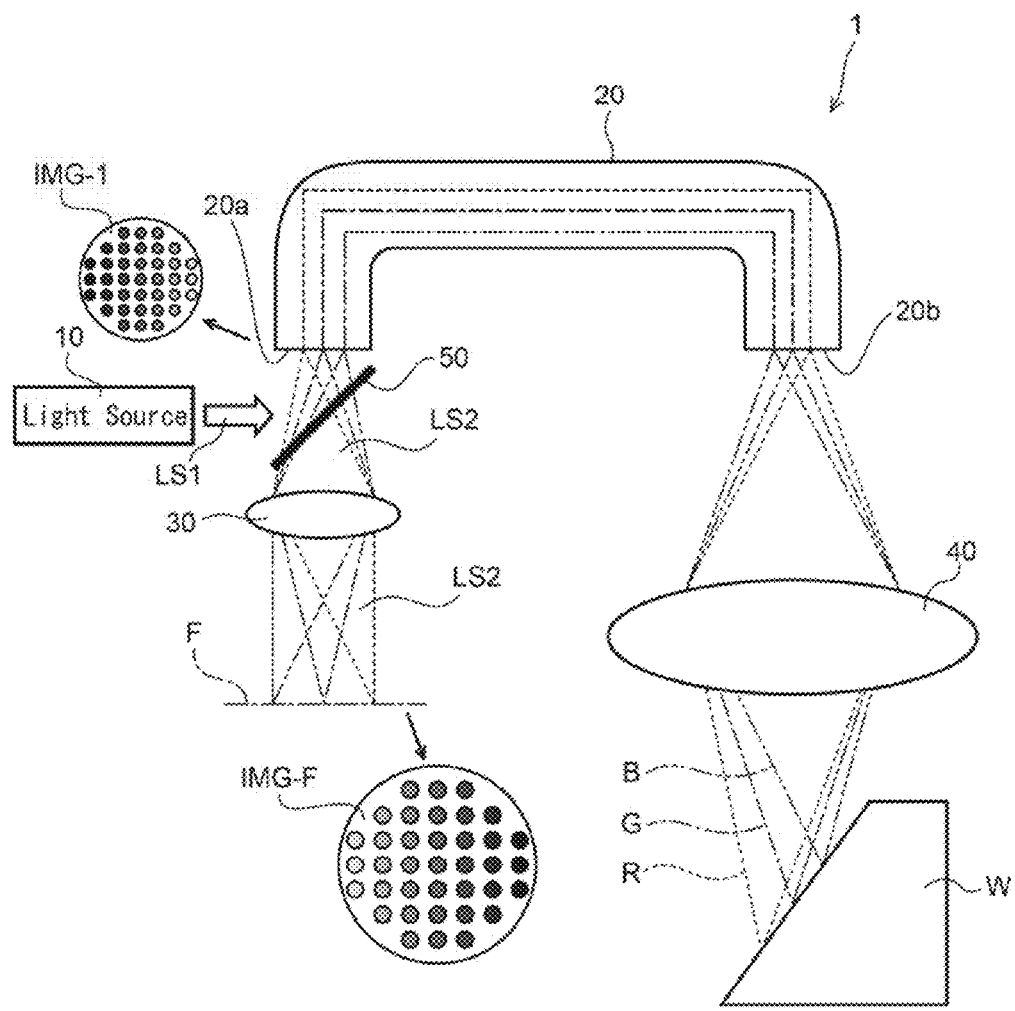
FIG. 1A is a configuration diagram of an optical observation apparatus according to a first embodiment.

Hereinafter, embodiments of the present invention will be described with reference to the drawings. Incidentally, in the following description, the same reference numerals are attached to the same parts, and descriptions regarding parts described once will not be repeated as appropriate.

First Embodiment

Figure 1B:
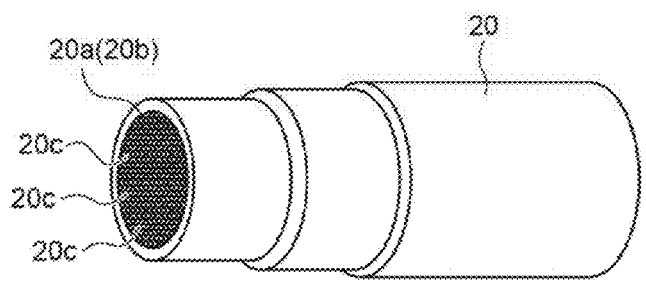
FIG. 1B is a configuration diagram of an image fiber.

FIGS. 1A and 1B are diagrams exemplifying an optical observation apparatus according to a first embodiment. FIG. 1A illustrates a configuration diagram of an optical observation apparatus 1 according to the first embodiment, and FIG. 1B illustrates a configuration diagram of an image fiber 20.

As illustrated in FIG. 1A, the optical observation apparatus 1 according to the present embodiment is provided with a light source 10, the image fiber 20, an imaging lens 30 which is an imaging optical system, and an objective lens 40 which is an axial aberration optical system. According to the optical observation apparatus 1, an image IMG-F focused over a wide range of a surface of a work W, which is an object to be observed, appears on an imaging plane F formed by the imaging lens 30.

The light source 10 emits broadband light. For example, a laser light source is used as the light source 21. The broadband light is white light, for example.

The image fiber 20 has a first end face 20a and a second end face 20b. FIG. 1B illustrates a configuration example of the image fiber 20. For convenience of description, FIG. 1B illustrates only one end face (for example, the first end face 20a) of the image fiber 20, but the other end face (for example, the second end face 20b) is formed likewise.

End faces of a plurality of cores 20c are two-dimensionally arrayed (for example, in a hexagonal close-packed array) in the first end face 20a of the image fiber 20. A diameter of the core 20c is about from 3 μm 5 μm. The number of the plurality of cores 20c is about from 3,000 to 30,000. The entire diameter of the plurality of cores 20c bundled is about from 0.4 mm to 8 mm.

The array of the end faces of the plurality of cores 20c is maintained from the first end face 20a to the second end face 20b. In this manner, the image fiber 20 can transmit a two-dimensional image incident from the second end face 20b to the first end face 20a while maintaining a shape thereof.

The imaging lens 30 is provided on the first end face 20a side of the image fiber 20. The imaging lens 30 causes light emitted from the first end face 20a of the image fiber 20 to be imaged on the imaging plane F. A lens having a small axial chromatic aberration is used as the imaging lens 30.

A beam splitter 50 is provided between the imaging lens 30 and the first end face 20a. The beam splitter 50 reflects the light emitted from the light source 10 to the first end face 20a side, and transmits the light emitted form the first end face 20a to the imaging lens 30 side.

The objective lens 40 is provided on the second end face 20b side of the image fiber 20. The objective lens 40 causes light emitted from the second end face 20b toward the work W to be converged. In the present embodiment, the objective lens 40 has a large axial chromatic aberration on an optical axis. In this manner, a focal length on the optical axis of the light emitted from the second end face 20b and passing through the objective lens 40 is different depending on the wavelength of the light. For example, in the objective lens 40, the focal length is short as the wavelength is short, and the focal length is long as the wavelength is long. Accordingly, among a blue light B, a green light G and a red light R, the focal length increases in order of the blue light B, the green light G and the red light R. Incidentally, in the objective lens 40, the relationship between the wavelength and the focal length may be opposite to the above description. In addition, a confocal position of the objective lens 40 is adjusted to the second end face 20b of the image fiber 20.

In the optical observation apparatus 1 provided with such a configuration, the image fiber 20 transmits the light emitted from the light source 10 from the first end face 20a to the second end face 20b. Further, the image fiber 20 takes the light (detected light), which is reflected and scattered by the surface of the work W, converged on the second end face 20b by the objective lens 40, and focused for each of the plurality of cores 20c, from the second end face 20b and transmits the light to the first end face 20a.

The detected light transmitted from the second end face 20b to the first end face 20a is imaged on the imaging plane F by the imaging lens 30 from the second end face 20b, and appears as the two-dimensional image IMG-F. A user of the optical observation apparatus 1 can refer to the image IMG-F of the surface of the work W using the imaging plane F as an observation plane.

In the optical observation apparatus 1, the surface of the work W is intensively irradiated with light having the focal length corresponding to the height of the surface (distance from the objective lens 40) using the axial chromatic aberration of the objective lens 40. Further, the detected light of the light is converged to the second end face 20b of the image fiber 20 by the objective lens 40. Since the second end face 20b matches with the confocal position of the objective lens 40, it is possible to take the entire light, with the wavelength having the focal length corresponding to the height of the work W, from the second end face 20b.

That is, each of the cores 20c of the second end face 20b is regarded as a pinhole arranged at the confocal position, and thus, each of the cores 20c is configured to take the focused light at each position of the cores 20c on the second end face 20b. The image fiber 20 puts together the light taken from the respective cores 20c to form an image and transmits the image from the second end face 20b to the first end face 20a. The image IMG-1 transmitted from the second end face 20b to the first end face 20a is projected onto the imaging plane F by the imaging lens 30. The image IMG-F projected onto the imaging plane F is an image of the surface of the work W.

The light configuring the image IMG-F includes a wavelength component depending on the height of the surface of the work W. Accordingly, the image IMG-F appearing on the imaging plane F is displayed in a state of being distinguishable according to the wavelength (color) depending on the height of the surface of the work W. In this manner, in the optical observation apparatus 1 according to the present embodiment, it is possible to easily obtain the image IMG-F being color-coded depending on the height of the surface of the work W without performing the image processing such as synthesizing the taken images.

Figure 2:
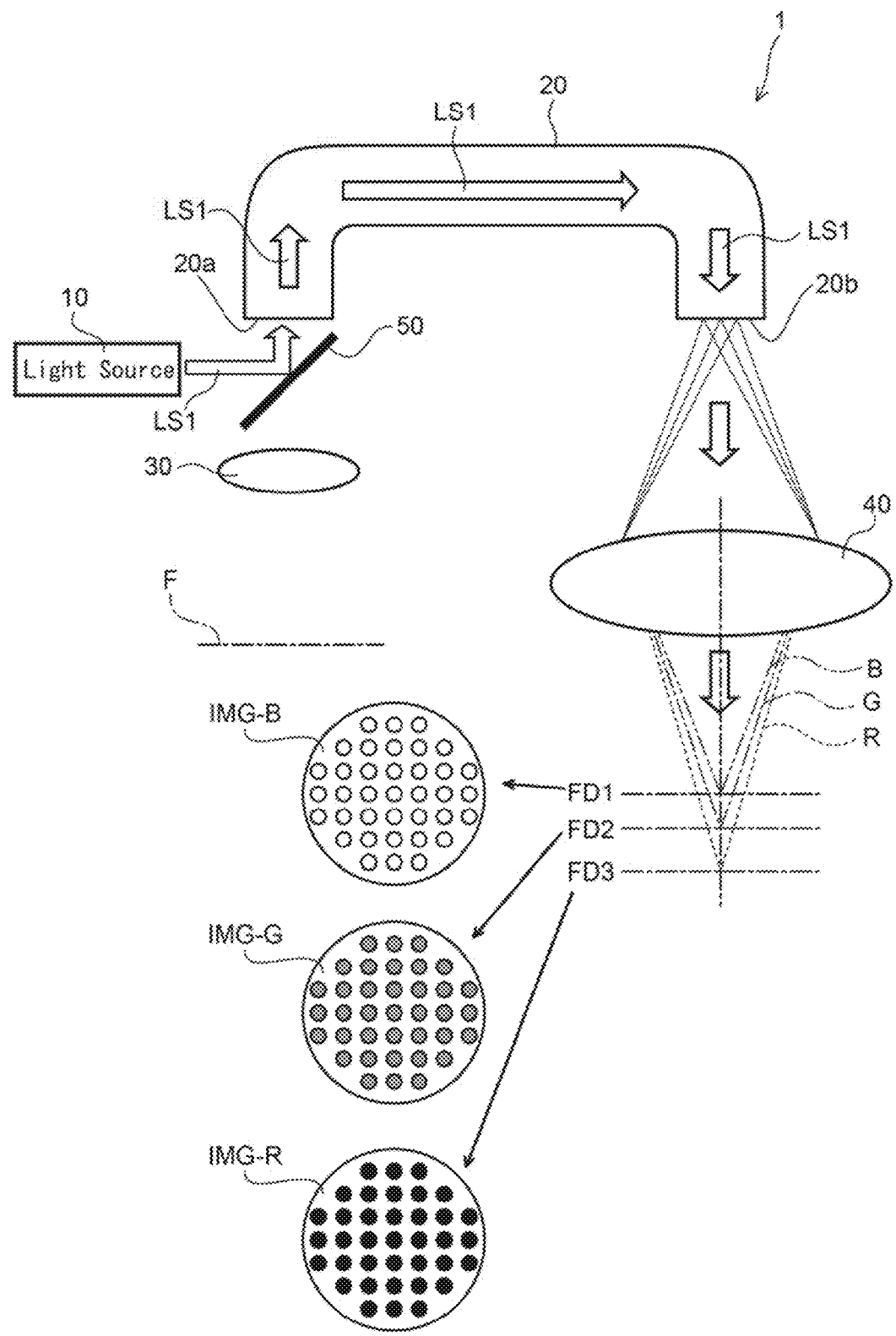
FIG. 2 is a schematic view (first one) exemplifying an optical observation method.
Figure 3:
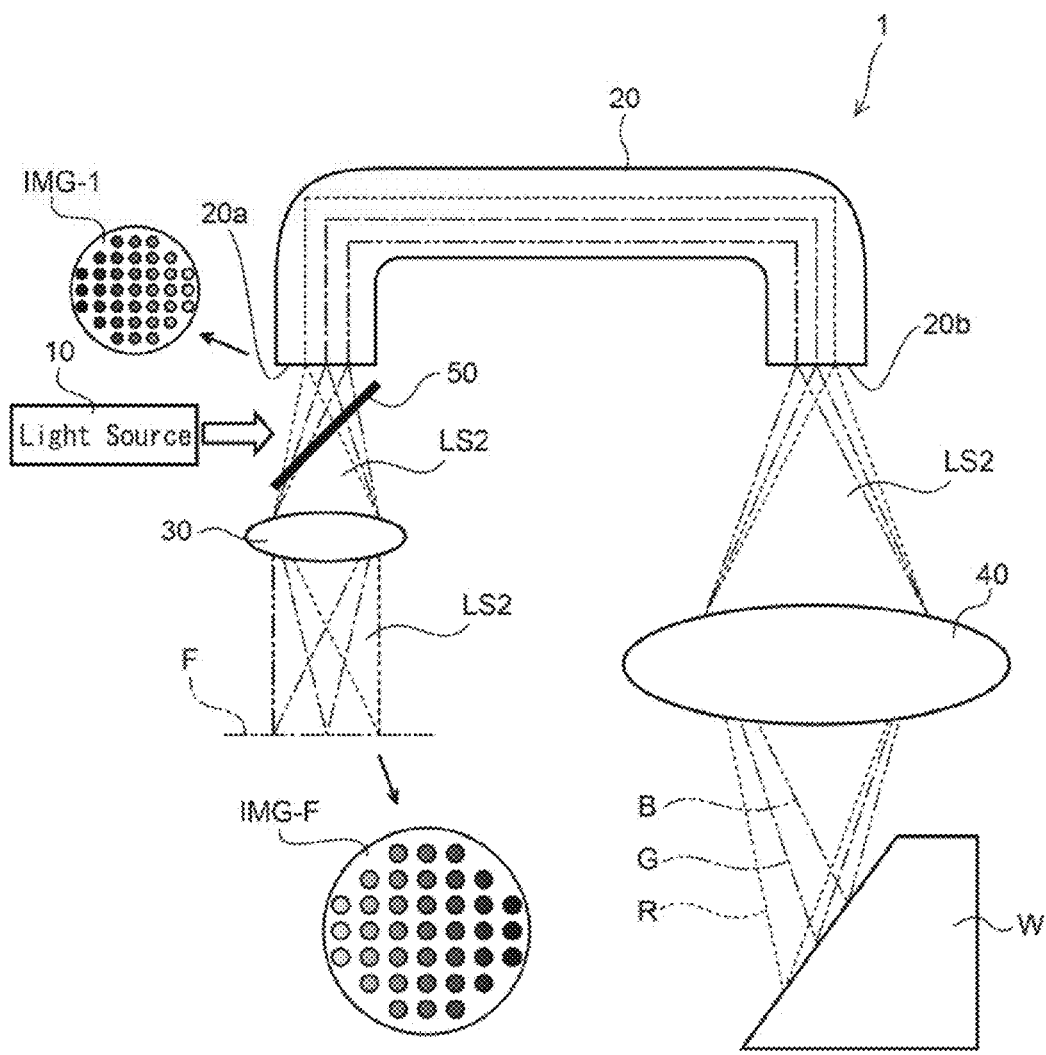
FIG. 3 is a schematic view (second one) exemplifying the optical observation method.

Next, the optical observation method will be described. In the following description, an observation method using the optical observation apparatus 1 according to the present embodiment will be exemplified. FIGS. 2 and 3 are schematic views exemplifying the optical observation method.

First, as illustrated in FIG. 2, a broadband light (for example, white light) LS1 is emitted from the light source 10. The broadband light LS1 is reflected by the beam splitter 50, and is taken into an inner side from the first end face 20a of the image fiber 20. The broadband light LS1 passes inside the plurality of cores 20c of the image fiber 20, and is emitted from the second end face 20b. The broadband light LS1 emitted from the second end face 20b is converged by the objective lens 40, and irradiated onto the work W.

Since the objective lens 40 has a large axial chromatic aberration, the focal length of the broadband light LS1 irradiated onto the work W by the objective lens 40 is different depending on the wavelength. For example, in a case where a focal length of the blue light B is set to FD1, a focal length of the green light G is set to FD2, and a focal length of the red light R is set to FD3, FD1<FD2<FD3.

Here, for example, in a case where a flat surface of the object to be observed is present at a position of the focal length FD1, an image of the image of the detected light is an image IMG-B of a blue color. In addition, in a case where the flat surface of the object to be observed is present at a position of the focal length FD2, the image of the detected light is an image IMG-G of a green color. In addition, in a case where the flat surface of the object to be observed is present at a position of the focal length FD3, the image of the detected light is an image IMG-R of a red color.

Next, as illustrated in FIG. 3, a detected light LS2, which is the light reflected and scattered by the surface of the broadband light LS1 irradiated onto the surface of the work W, is converged on the second end face 20b of the image fiber 20 by the objective lens 40. The light focused for each of the cores 20c on the second end face 20b contains a lot of wavelength components of the light focused on the surface of the work W. In other words, the light with the wavelength having the focal length corresponding to the height of the surface of the work W is intensively converged for each of the cores 20c, and the converged light reaches the second end face 20b. Thus, an image of the detected light LS2 reaching the second end face 20b includes information of the wavelength corresponding to the height of the surface of the work W. Further, the detected light LS2 is transmitted from the second end face 20b to the first end face 20a.

The detected light LS2 transmitted to the first end face 20a is imaged on the imaging plane F by the imaging lens 30. The image IMG-F of the surface of the work W appears on the imaging plane F. The image IMG-F includes information of the wavelength corresponding to the height of the surface of the work W. Accordingly, it is possible to observe the surface of the work W using the image IMG-F, and to grasp the height of the surface of the work W according to the wavelength (color) of the image IMG-F.

A range in which the height of the work W is distinguishable according to the wavelength (color) becomes a range of the wavelength of the broadband light. Accordingly, when the white light is used as the broadband light, the color coding of the height of the work W is possible in a range of the focal length of the objective lens 40 corresponding to a range of wavelengths of the white light.

For example, as illustrated in FIG. 3, in a case where an inclined surface of the work W is observed, the image IMG-F of which color is changed along the inclination is projected on the imaging plane F. Although the image IMG-F of the surface of the work W to be projected on the imaging plane F is flat, it is possible to grasp the height of the surface of the work W according to the color corresponding to the inclination (height).

Figure 4A:
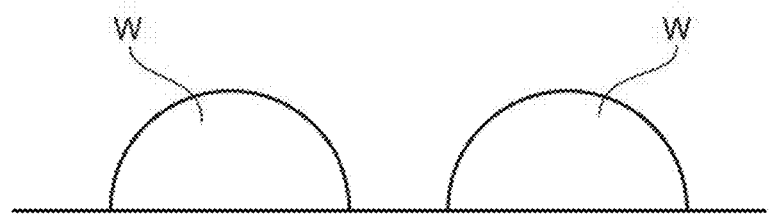
FIG. 4A is a schematic view exemplifying a work including a hemispherical convex portion
Figure 4B:
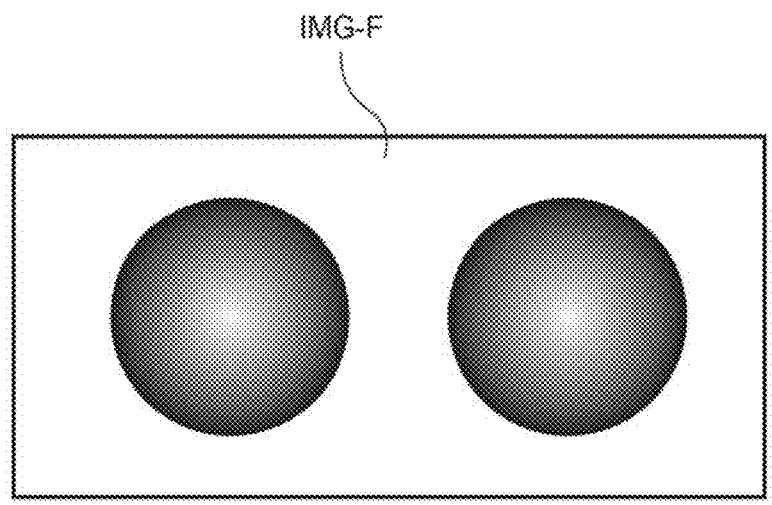
FIG. 4B is a schematic view illustrating an observation example.

In addition, for example, in a case where the work W including the hemispherical convex portion as illustrated in FIG. 4A, a surface part of the convex portion in the image IMG-F appearing on the imaging plane F is projected in a state of being color-coded in a concentric circle depending on the height of the hemisphere (see FIG. 4B). In this manner, an observer can easily grasp a state of the surface of the work W by the image IMG-F to be projected on the imaging plane F, and the height of the surface of the work W according to the color.

Second Embodiment

Next, an optical observation apparatus according to a second embodiment will be described.

Figure 5A:
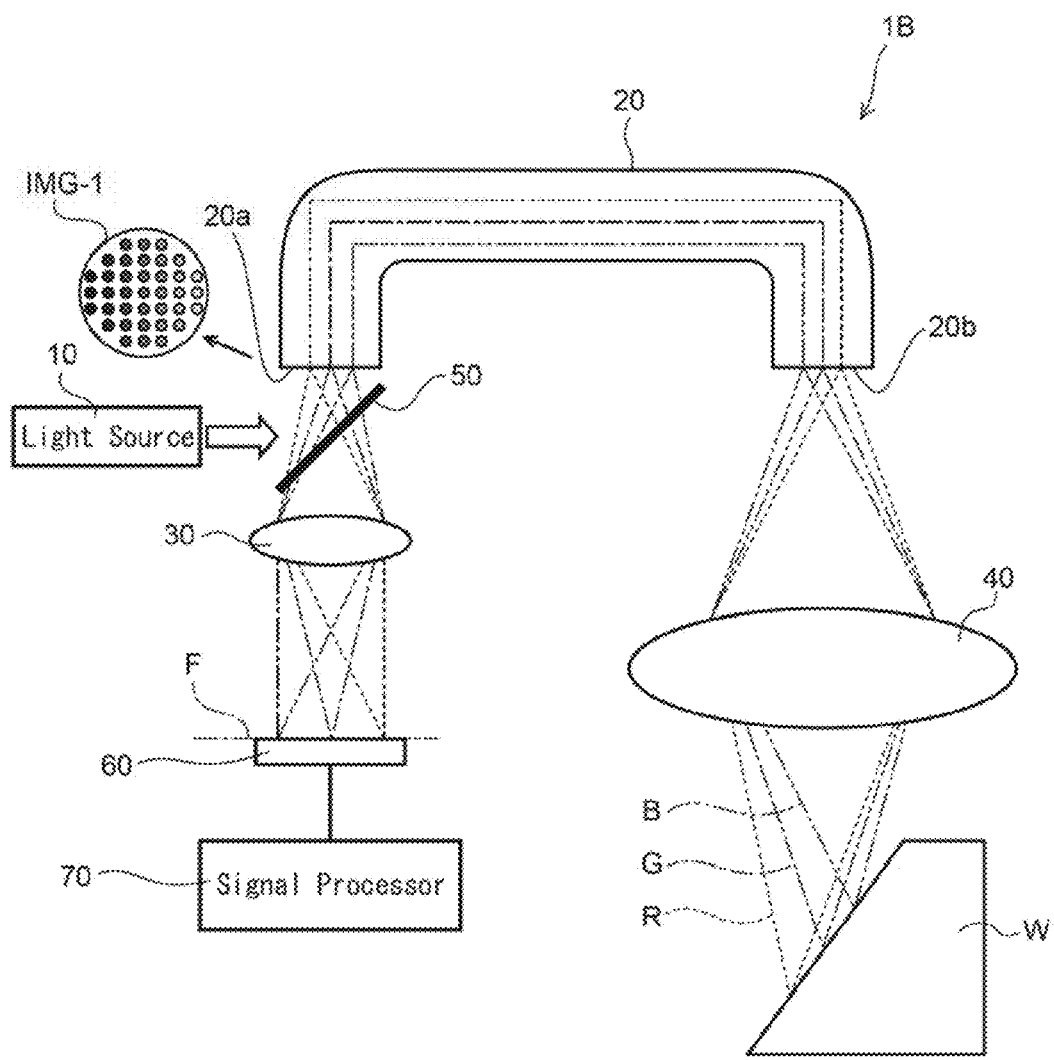
FIG. 5A is a configuration diagram of the optical observation apparatus according to the first embodiment.
Figure 5B:
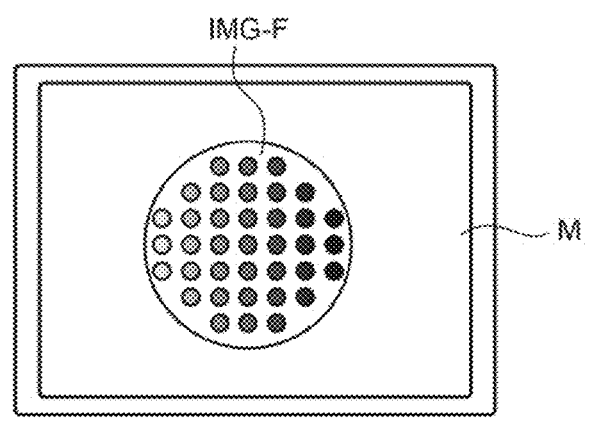
FIG. 5B is a schematic view illustrating a display example of a monitor.

FIGS. 5A and 5B are diagrams exemplifying the optical observation apparatus according to the second embodiment. FIG. 5A illustrates a configuration diagram of an optical observation apparatus 1B according to the second embodiment, and FIG. 5B illustrates a display example of a monitor M.

As illustrated in FIG. 5A, the optical observation apparatus 1B according to the second embodiment is provided with an image pickup section 60 positioned on the imaging plane F, and a signal processor 70. The other configurations are the same as those of the optical observation apparatus 1 according to the present embodiment.

In the optical observation apparatus 1B, the light imaged on the imaging plane F by the imaging lens 30 is taken by the image pickup section 60. A charge coupled device (CCD), a complementary metal-oxide semiconductor (CMOS), or the like is used as the image pickup section 60. The image IMG-F formed based on the light taken by the image pickup section 60 is displayed on the monitor M as illustrated in FIG. 5B.

In addition, the signal processor 70 performs a predetermined processing with respect to a signal for each pixel taken by the image pickup section 60. For example, a peak wavelength of a predetermined area (for example, for each pixel) of the light taken by the image pickup section 60 is detected and the focal length of the objective lens 40 corresponding to the detected peak wavelength is obtained. Further, the height of the surface of the work W corresponding to a position of the predetermined area is obtained from the focal length. In this manner, it is possible to obtain the height of the surface of the work W corresponding to the predetermined area of the image pickup section 60 as a numerical value. Further, it is possible to acquire information of a three-dimensional shape of the surface of the work W from data obtained by digitizing the height of the surface of the work W.

Application Example

In the optical observation apparatuses 1 and 1B, and the optical observation method described above, the broadband light LS1 to be irradiated onto the work W may be spot light or line light. In addition, a relative position between the broadband light LS1 and the work W may be varied (scanned). For example, when the relative position between the line light and the work W is scanned in a direction perpendicular to a line direction, it is possible to grasp the three-dimensional shape of the surface of the work W in a wide range.

As described above, according to the embodiments, it is possible to provide the optical observation apparatuses 1 and 1B, and the optical observation method capable of easily acquiring the all-in-focus image of the object to be observed, and further visually grasping the height of each portion of the surface.

Incidentally, although the embodiments and the application example thereof are described as above, the present invention is not limited to these examples. For example, anything obtained by appropriately performing addition, removal or design alteration of a component with respect to the embodiments and the application example described above by a person skilled in the art is included in a range of the present invention as long as containing a gist of the present invention.

What is claimed is:

1. An optical observation apparatus comprising:
a light source emitting broadband light;
an image fiber with a first end face and a second end face, in which end faces of a plurality of cores are two-dimensionally arrayed in the first end face and the second end face;
an imaging optical system provided on the first end face side of the image fiber, arranged between the first end face and an imaging plane, and causing light emitted from the first end face to be imaged on the imaging plane; and
an axial aberration optical system provided on the second end face side of the image fiber, arranged so that a confocal position of the axial aberration optical system is located at the second end face of the image fiber, having an axial chromatic aberration on an optical axis, and causing light emitted from the second end face toward an object to be observed to be converged,
wherein the image fiber takes the light emitted from the light source from the first end face, and transmits the light to the second end face, and takes the light, which is reflected and scattered by a surface of the object to be observed, converged by the axial aberration optical system, and focused for each of the plurality of cores on the second end face, from the second end face and transmits the light to the first end face, and
wherein the imaging optical system causes the light emitted from the first end face to be imaged on the imaging plane so as to appear as an image containing a wavelength component depending on a height of the object to be observed.

2. The optical observation apparatus according to claim 1, wherein the axial aberration optical system causes light, with a wavelength to be focused onto the surface of the object to be observed among light emitted from each of the plurality of cores and reflected and scattered by the surface of the object to be observed, to be imaged on the core of an emission source on the second end face.

3. The optical observation apparatus according to claim 1, wherein the imaging optical system causes the light with a wavelength, which corresponds to a distance between the axial aberration optical system and the object to be observed, to be imaged on the imaging plane.

4. The optical observation apparatus according to claim 1, wherein the light source is a white light source.

5. An optical observation method comprising:
irradiating an object to be observed with broadband light by an axial aberration optical system having an axial chromatic aberration;
taking, by an image fiber with a first end face and a second end face in which end faces of a plurality of cores are two-dimensionally arrayed in the first end face and the second end face, light which is reflected and scattered by a surface of the object to be observed, converged by the axial aberration optical system, and focused for each of the plurality of cores on the second end face, and transmitting the taken light to the first end face; and
causing light emitted from the first end face to be imaged on an imaging plane by an imaging optical system, so as to appear as an image containing a wavelength component depending on a height of the object to be observed, wherein:
the imaging optical system is arranged between the first end face and the imaging plane,
the axial aberration optical system is arranged so that a confocal position of the axial aberration optical system is located at the second end face of the image fiber.

* * * * *